(12) United States Patent
Miller et al.

(10) Patent No.: US 11,690,511 B2
(45) Date of Patent: Jul. 4, 2023

(54) POLARIZATION FILTERING FOR IMPROVED EYE IMAGING

(71) Applicant: LUTRONIC VISION INC., Burlington, MA (US)

(72) Inventors: Seth Adrian Miller, Longmont, CO (US); Mark Meloni, Longmont, CO (US)

(73) Assignee: LUTRONIC VISION INC., Burlington, MA (US)

( * ) Notice: Subject to any disclaimer, the term of this patent is extended or adjusted under 35 U.S.C. 154(b) by 328 days.

(21) Appl. No.: 16/767,555

(22) PCT Filed: Dec. 1, 2017

(86) PCT No.: PCT/US2017/064217
§ 371 (c)(1),
(2) Date: May 27, 2020

(87) PCT Pub. No.: WO2019/108227
PCT Pub. Date: Jun. 6, 2019

(65) Prior Publication Data
US 2020/0367746 A1    Nov. 26, 2020

(51) Int. Cl.
*A61B 3/14*        (2006.01)
*A61B 3/00*        (2006.01)
(Continued)

(52) U.S. Cl.
CPC .............. *A61B 3/14* (2013.01); *A61B 3/0008* (2013.01); *A61B 3/12* (2013.01); *A61F 9/008* (2013.01);
(Continued)

(58) Field of Classification Search
None
See application file for complete search history.

(56) References Cited

U.S. PATENT DOCUMENTS

| 6,086,204 A | 7/2000 | Magnante |
| 7,967,440 B1 | 6/2011 | Copland et al. |

(Continued)

FOREIGN PATENT DOCUMENTS

WO     2011091434 A1    7/2011

OTHER PUBLICATIONS

International Search Report and Witten Opinion for International Application No. PCT/US2017/064217 dated Feb. 9, 2018, pp. 18.
(Continued)

*Primary Examiner* — Kyle Zhai

(57) ABSTRACT

An optical device can include: an incident light polarizer positioned to receive incident light and configured to polarize incident light such that polarized incident light is directed to a cornea of a subject; at least one corneal light polarizer, wherein the at least one corneal light polarizer is positioned to receive reflected light from the cornea of the subject and polarize the reflected light to a second polarization; at least one rotating mechanism; and at least one receiver. The receiver can be at least one viewing port optically coupled with the at least one corneal light polarizer or an imaging device (e.g., optical detector). The at least one rotating mechanism is: coupled with the incident light polarizer; coupled with the at least one corneal light polarizer; or coupled with the incident light polarizer and the at least one corneal light polarizer.

13 Claims, 8 Drawing Sheets

(51) Int. Cl.
  *A61B 3/12* (2006.01)
  *A61F 9/008* (2006.01)
  *G02B 5/30* (2006.01)

(52) U.S. Cl.
  CPC .. *G02B 5/3066* (2013.01); *A61F 2009/00872* (2013.01)

(56) References Cited

U.S. PATENT DOCUMENTS

| | | |
|---|---|---|
| 8,328,357 B2 | 12/2012 | Davis |
| 2006/0146284 A1 | 7/2006 | Collins et al. |
| 2007/0123761 A1* | 5/2007 | Daly .................... A61B 3/1005 600/319 |
| 2007/0146632 A1 | 6/2007 | Chipman |
| 2008/0319427 A1 | 12/2008 | Palanker |
| 2010/0073756 A1* | 3/2010 | Moskovits ............. G02B 27/28 359/290 |
| 2010/0097682 A1 | 4/2010 | Angeley et al. |
| 2011/0098692 A1* | 4/2011 | Shazly .................. A61F 9/008 606/10 |
| 2011/0237999 A1 | 9/2011 | Muller et al. |
| 2013/0321770 A1 | 12/2013 | Mizuno |
| 2014/0016093 A1 | 1/2014 | Korb et al. |
| 2014/0071424 A1* | 3/2014 | Dunne .................... G01C 3/04 356/3 |
| 2015/0018661 A1* | 1/2015 | Yen ....................... A61B 3/165 600/401 |
| 2015/0366714 A1 | 12/2015 | Kandavel et al. |
| 2016/0296112 A1 | 10/2016 | Fletcher et al. |
| 2017/0105620 A1 | 4/2017 | Charles |

OTHER PUBLICATIONS

"Polarizer," Wikipedia, accessed at https://web.archive.org/web/20170725055718/https://en.wikipedia.org/wiki/Polarizer, last edited on Jul. 4, 2017, pp. 13.

Clark, B.A.J., and Carney, L.G., "Refractive Index and Reflectance of the Anterior Surface of the Cornea," American journal of optometry and archives of American Academy of Optometry, vol. 48, No. 4, pp. 333-343 (Oct. 1971).

Heinzelmann, S., et al., "Correlation between visual acuity and interface reflectivity measured by pentacam following DSAEK," Acta ophthalmologica, vol. 92, No. 1, pp. 4 (Jul. 26, 2013).

Knighton, R.W., and Huang, X-R., "Linear birefringence of the central human cornea," Investigative ophthalmology & visual science, vol. 43, No. 1, pp. 82-86 (Feb. 2002).

Preece, S.J., and Claridge, E., "Monte Carlo modelling of the spectral reflectance of the human eye," Physics in Medicine and Biology, vol. 47, No. 16, pp. 2863-2877 (Jul. 24, 2002).

* cited by examiner

POLARIZATION FILTERING FOR IMPROVED EYE IMAGING

CROSS-REFERENCE

This patent application is section 371 nationalization of PCT Application No. PCT/US2017/064217 filed Dec. 1, 2017, which application is incorporated herein by specific reference in its entirety.

BACKGROUND

In a standard laser eye surgery system, the ophthalmologist is presented with an optical image of the eye surgical site to allow for properly positioning the laser to target the desired areas of the eye. The surgical sight may be the cornea for a laser-assisted in situ kartomileusis (LASIK). Another example may be an R:GEN laser system for performing selective retinal therapy (SRT) for treatment of clinically significant macular edema (CSME) which is a condition secondary to diabetic retinopathy. Since the retinal pigment epithelium (RPE) layer and choroid of the eye are rich in melanin, in order to absorb light, the reflectivity of the eye RPE surgical sites are quite low. For example, the reflectivity of light from the back of the eye can be from 1-10% depending on the wavelength used and the eye color of the patient. However, reflections from the front surface of the cornea (e.g., corneal anterior surface) can be significant.

Optically imaging an eye surgical site, such as the RPE, has previously been challenging because light reflecting off the absorbing eye surgical site is mixed with light reflected off the air-cornea interface (e.g., corneal anterior surface). The refractive index of the cornea is approximately 1.38, giving a calculated surface reflection of about 2.5% for normally incident light. However, the actual reflectivity can be higher, such as up to 8%, due to scattering from other internal layers of the eye. Accordingly, a light source can be reflected off of a human corneal anterior surface, where a reflected "glint" and the darkness of the retinal surface can be observed. An estimate of the contrast ratio based upon an averaged 8% reflection from the cornea and a 5% reflection from the retina is found to have a small contrast ratio, such that there is little contrast when imaging the eye, whether imaging with a device or visually by a naked eye (e.g., of an ophthalmologist).

Accordingly, it can be helpful to reduce corneal reflections and improve contrast when imaging or visualizing specific areas of the eye.

SUMMARY

In one embodiment, an optical device can include: an incident light polarizer positioned to receive incident light and configured to polarize incident light such that polarized incident light is directed to a cornea of a subject; at least one corneal light polarizer, wherein the at least one corneal light polarizer is positioned to receive reflected light from the cornea of the subject and polarize the reflected light to a second polarization; at least one rotating mechanism; and at least one receiver. In one aspect, the receiver can be at least one viewing port optically coupled with the at least one corneal light polarizer or an imaging device (e.g., optical detector). In one aspect, the at least one rotating mechanism is: coupled with the incident light polarizer; coupled with the at least one corneal light polarizer; or coupled with the incident light polarizer and the at least one corneal light polarizer. In one aspect, the incident light polarizer is configured to polarize light to a first polarization in an illumination path directed to a cornea of a subject. In one aspect, the at least one corneal light polarizer is positioned to receive reflected light from the cornea of a subject and polarize the reflected light to a second polarization, wherein the reflected light is from the incident light and incident light polarizer. In one aspect, the at least one rotating mechanism is coupled with the incident light polarizer. In one aspect, the at least one rotating mechanism is coupled with the at least one corneal light polarizer. In one aspect, the at least one rotating mechanism includes a first rotating mechanism coupled with the incident light polarizer and includes at least one second rotating mechanism that is coupled with the at least one corneal light polarizer. In one aspect, the incident light polarizer and the at least one corneal light polarizer are a linear polarizer or circular polarizer.

In one embodiment, the at least one viewing port includes at least one eyepiece (e.g., ocular piece). In one aspect, each eyepiece of the at least one eyepiece includes at least one lens. In one aspect, the eyepiece can include an eyepiece objective having the at least one lens. In one aspect, at least one viewing port is configured for viewing with an eye.

In one embodiment, the optical device can include a light source configured to provide the incident light. In one aspect, a light emitter is included in the light source. In one aspect, the light emitter is a light emitting diode (LED). In one aspect, at least one lens is included in the light source that is optically coupled with the light emitter. In one aspect, at least one mirror is included in the light source that is optically coupled with the light emitter. In one aspect, at least one mirror is included in the light source optically coupled with the light emitter and the at least one lens. In one aspect, an optical aperture device having an optical aperture is included in the light source that is optically coupled with the light emitter. In one aspect, the light source includes a housing containing the light emitter.

In one embodiment, a housing contains the incident light polarizer, the at least one corneal light polarizer, and the at least one rotating mechanism. However, the housing may include other components or the other components may be operably or directly coupled with the housing.

In one embodiment, the optical device can include additional components. In one aspect, the optical device can include at least one safety filter positioned such that the reflected light passes through the at least one safety filter before the at least one viewing port or receiver. In one aspect, the at least one corneal light polarizer is between the at least one safety filter and the at least one viewing port or receiver. In one aspect, the at least one safety filter is between the at least one corneal light polarizer and the at least one viewing port or receiver. In one aspect, an optical objective is positioned such that the reflected light passes through the optical objective before the at least one viewing port or receiver. In one aspect, the optical objective is positioned such that the reflected light passes through the optical objective before the at least one corneal light polarizer. In one aspect, a lens is positioned such that the reflected light passes through the lens before the at least one viewing port. In one aspect, the lens is positioned such that the reflected light passes through the lens before the at least one corneal light polarizer. In one aspect, a convergent lens is positioned such that the reflected light passes through the convergent lens before the at least one viewing port. In one aspect, the convergent lens is positioned such that the reflected light passes through the convergent lens before the at least one corneal light polarizer. In one aspect, a lens series is included that has a convergent lens and: at least one right eye lens positioned such that the reflected light passes through the convergent lens and the at least one right eye lens before a right eye viewing port of the at least one viewing port; and/or at least one left eye lens positioned such that the reflected light passes through the convergent lens and the at least one left eye lens before a left eye viewing port of the at least one viewing port. In one aspect, a lens series can have a convergent lens and: at least one right eye lens positioned such that the reflected light passes through the convergent lens and the at least one right eye lens before the at least one corneal light polarizer; and/or at least one left eye lens positioned such that the reflected light passes through the convergent lens and the at least one left eye lens before the at least one corneal light polarizer.

In one embodiment, the optical device can include a laser port positioned to receive the reflected light from the cornea of the subject. In one aspect, a laser mirror is positioned to receive the reflected light from the cornea of the subject and reflect the reflected light to the laser port. In one aspect, a collimating lens is positioned to receive the reflected light from the cornea of the subject and configured to provide collimated light to the laser port.

In one embodiment, a controller is operably coupled with the at least one rotating mechanism, the controller being configured to control rotation of the at least one rotating mechanism so as to control rotation of one of: the incident light polarizer; the at least one corneal light polarizer; or the incident light polarizer and the at least one corneal light polarizer independently of each other.

In one embodiment, a window is positioned to receive the reflected light from the cornea of the subject and positioned such that the reflected light passes through the window before at least one of an optical objective, convergent lens, lens series, right eye lens, left eye lens, or laser mirror.

In one embodiment, at least one beam splitter is positioned between the at least one corneal light polarizer and at least one viewing port or other receiver. In one aspect, at least one detector is positioned such that a split portion of the reflected light from the cornea of the subject by the at least one beam splitter is received by the at least one detector. In one aspect, the at least one beam splitter includes a right eye beam splitter and a left eye beam splitter and the at least one detector includes a near infrared detector and a color detector. In one aspect, the optical device can include at least one of: a right collimating lens between the right eye beam splitter and one of the near infrared detector and color detector; a right mirror between the right eye beam splitter and one of the near infrared detector and color detector; a left collimating lens between the left eye beam splitter and one of the near infrared detector and color detector; or a left mirror between the left eye beam splitter and one of the near infrared detector and color detector.

In one embodiment, the optical device includes a laser module. In one aspect, the laser module includes a laser emitter. In one aspect, the laser module includes a detector associated with the laser emitter such that the laser emitter and detector have a common optical direction.

In one embodiment, the optical device includes an eyepiece adapted for association with an eye of the subject, the eye having the cornea. The eyepiece is adapted to be positioned on the eye of the subject receiving the procedure.

In one embodiment, a laser eye surgery method can include: providing the optical device of one of the embodiments; associating the optical device with an eye of the subject, the eye having the cornea and retina; directing the polarized light with the first polarization to the cornea and to a retina; receiving the reflected light from the cornea and from the retina into the at least one corneal light polarizer, wherein the reflected light from the cornea has the first polarization and the reflected light from the retina has a different polarization from the first polarization; and polarizing the reflected light from the cornea having the first polarization with the at least one corneal light polarizer so as to obtain attenuated corneal light, and polarizing the reflected light from the retina having the different polarization with the at least one corneal light polarizer so as to obtain attenuated retinal light, wherein the attenuated corneal light has less intensity than the attenuated retinal light. In one aspect, the method includes positioning the incident light polarizer to a polarization direction that is crossed with a polarization direction of the at least one corneal light polarizer so that the attenuated corneal light is substantially extinguished. In one aspect, the method includes rotating the incident light polarizer. In one aspect, the method includes rotating the at least one corneal light polarizer. In one aspect, the method includes independently rotating the incident light polarizer and independently rotating the corneal light polarizer. In one aspect, the method includes marking a target position of the eye, such as the retina. In one aspect, the method includes positioning a laser module relative to the marked target position of the eye. In one aspect, the method includes performing laser eye surgery on the eye with the laser module. In one aspect, the method includes adjusting a polarization angle of the polarized light by rotating the incident light polarizer. In one aspect, the method includes increasing the contrast of an image of the retina by adjusting a difference in intensity of the attenuated corneal anterior surface light compared to the attenuated retinal light. In one aspect, the method includes filtering out the corneal light with the at least one corneal light polarizer.

In one embodiment, a method of improving eye image contrast during eye imaging can include: providing an optical device of one of the embodiments; associating the optical device with an eye of the subject, the eye having the cornea; directing the polarized light with the first polarization to the cornea and to a retina; receiving the reflected light from the cornea and from the retina into the at least one corneal light polarizer, wherein the reflected light from the cornea has the first polarization and the reflected light from the retina has a different polarization from the first polarization; and polarizing the reflected light from the cornea having the first polarization with the at least one corneal light polarizer so as to obtain attenuated corneal light, and polarizing the reflected light from the retina having the different polarization with the at least one corneal light polarizer so as to obtain attenuated retinal light, wherein the attenuated corneal light has less intensity than the attenuated retinal light. In one aspect, the method includes positioning the incident light polarizer to have a polarization direction that is crossed with a polarization direction of the at least one corneal light polarizer so that the attenuated corneal light is substantially extinguished. In one aspect, the method includes rotating the incident light polarizer. In one aspect, the method includes rotating the at least one corneal light polarizer. In one aspect, the method includes independently rotating the incident light polarizer and independently rotating the corneal light polarizer. In one aspect, the method includes marking a target position of the eye, such as the retina. In one aspect, the method includes adjusting a polarization angle of the polarized light by rotating the incident light polarizer. In one aspect, the method includes increasing the contrast of an image of the retina by adjusting a difference in intensity of the attenuated corneal light compared to the attenuated retina. In one aspect, the method includes filtering out the corneal light with the at least one corneal light polarizer.

In some embodiments, an optical device can include: an incident light polarizer positioned to polarize incident light is directed to a cornea of a subject, wherein the polarized incident light has a first polarization; at least one corneal light polarizer is positioned to polarize reflected light from the cornea of the subject to a second polarization that is different from the first polarization; a first rotating mechanism coupled with the incident light polarizer; at least one second rotating mechanism coupled with the at least one corneal light polarizer; and at least one viewing port optically coupled with the at least one corneal light polarizer.

In some embodiments, the optical device can include a mirror positioned to reflect a portion of the reflected light; and a laser port positioned to receive the reflected portion of the reflected light from the mirror.

In some embodiments, the optical device can include a controller operably coupled with the first rotating mechanism and the at least one second rotating mechanism, wherein the controller is configured to control rotation of the incident light polarizer and the at least one corneal light polarizer independently of each other.

In some embodiments, the optical device can include: a mirror positioned to reflect a portion of the reflected light; a laser port positioned to receive the reflected portion of the reflected light from the mirror; and a laser module having a laser emitter and a detector optically coupled with the laser port to receive the reflected light from the laser.

In some embodiments, a laser procedure system can include: an optical device comprising: an incident light polarizer positioned to polarize incident light that is directed to a cornea of a subject, wherein the polarized incident light has a first polarization; at least one corneal light polarizer positioned to polarize reflected light from the cornea of the subject to a second polarization that is different from the first polarization; a first rotating mechanism coupled with the incident light polarizer; at least one second rotating mechanism coupled with the at least one corneal light polarizer; and at least one viewing port optically coupled with the at least one corneal light polarizer; an eyepiece adapted for association with an eye of the subject; and a laser module optically coupled with the eyepiece.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

Figure 1:
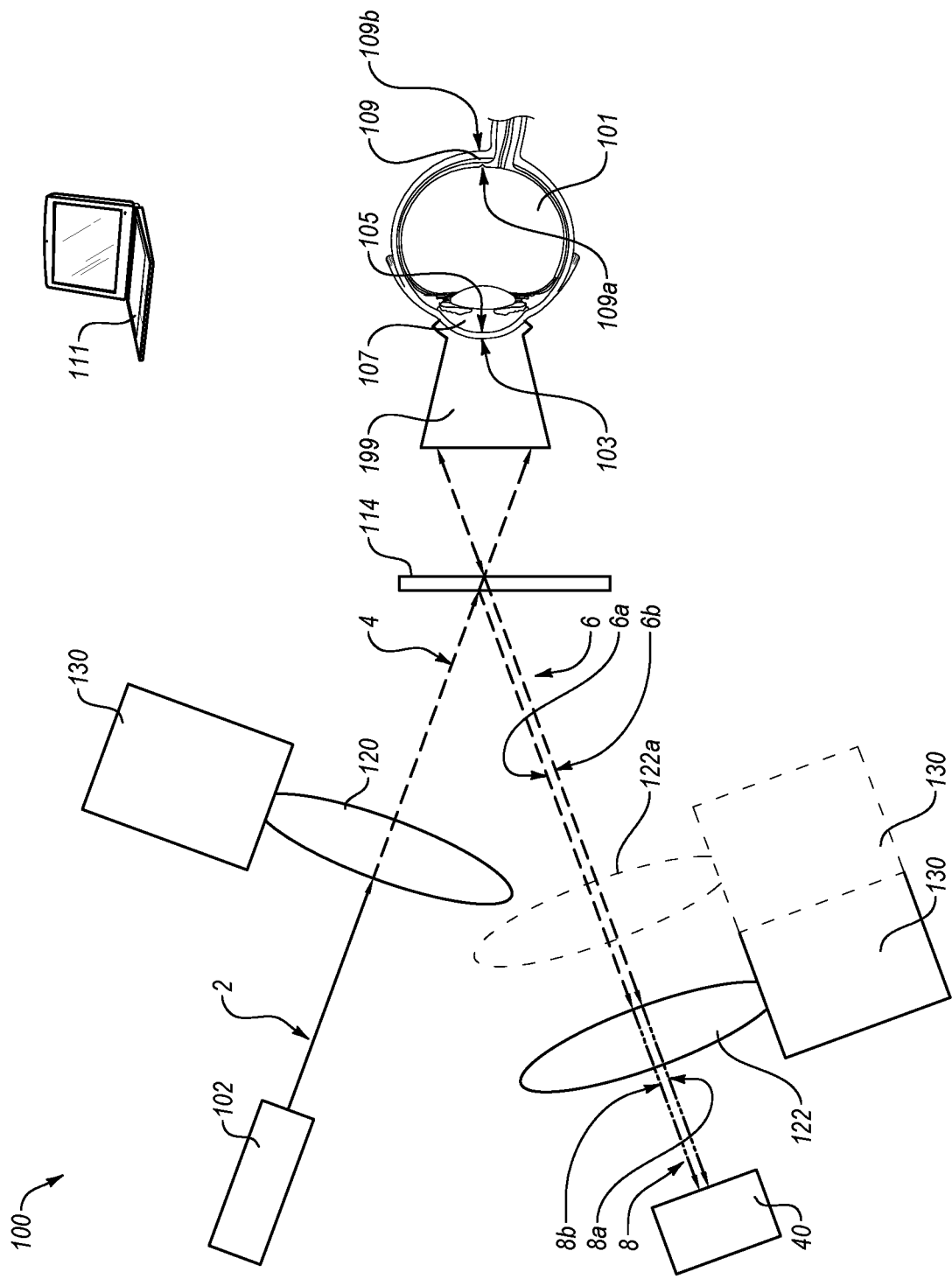
FIG. 1 illustrates an embodiment of an optical system.

The components in the figures are arranged in accordance with at least one of the embodiments described herein, and which arrangement may be modified in accordance with the disclosure provided herein by one of ordinary skill in the art. Components in one figure may be included in embodiments of other figures as appropriate.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology can reduce reflections of light from a cornea of an eye. The reduced reflections from the cornea can improve a contrast ratio (e.g., reduce the contrast ratio) from the cornea and retina, which can improve imaging of an eye (e.g., retina) with an eye imaging device or imaging by an ophthalmologist or other eye imaging professional. By reducing reflections from the cornea, an ophthalmologist or eye surgeon can have an improved optical view of an RPE in the eye. Thus, the present technology can improve contrast during eye viewing, eye imaging, or acquiring eye images, which may be of the RPE.

In one embodiment, devices, systems having the devices, and method of using the devices and/or systems is provided to reduce reflections of light from a cornea of an eye. In one aspect, the reduced reflections from the cornea can be for improving a contrast ratio of the cornea and retina. In one aspect, the reduced reflections from the cornea can be used for improving viewing or imaging of a specific area of an eye, such as the RPE or other area. In one aspect, the reduced reflections from the cornea can be used for improving an optical view of an RPE or other surgical site in the eye. In one aspect, the reduced reflections from the cornea can be used for improving eye viewing, eye imaging, or acquiring eye images, as well as any medical procedure performed on the eye, such as eye surgery (e.g., laser eye surgery, such as R:GEN laser eye surgery). However, any optical imaging with a device or viewing with a naked eye can be improved by reducing reflections from the cornea, which can be for any purpose or method. In one aspect, the specific area of the eye being imaged is the retina, such as the RPE.

In one embodiment, the reduced reflections from the cornea can be obtained by filtering out light reflected from the front surface (e.g., anterior surface) of the cornea at the cornea-air interface, which is at the exterior surface of the corneal epithelium. For anatomical reference, the cornea is considered to include the following layers from the outside (anterior) to inside (posterior): corneal epithelium (e.g., anterior surface) extending from the front surface to the Bowman's membrane; the Bowman's membrane extending from the corneal epithelium to the corneal stroma; the corneal stroma extending from the Bowman's membrane to the Descemet's membrane; the Descemet's membrane extending from the corneal stroma to the corneal endothelium; and the corneal endothelium extending from the Descemet's membrane to the back surface (e.g., posterior surface) of the cornea.

In one embodiment, a combination of two polarizers can be used to filter out reflected light in order to reduce reflections from the cornea. While two polarizers are used, incident light that is already polarized before entering the eye may be polarized with the second polarizer in the device and methods described herein because the incident light may be pre-polarized to provide the first polarization (e.g., first polarization of un-polarized light). The combination of the two polarizers can function to reduce reflections from the cornea due to the birefringent character of the eye, such as birefringence of the cornea or other portions of the eye. For example, polarized light entering the cornea can rotate due to the birefringent properties of the eye, with the median rotation of about 10-20° for a double-pass of light, which double passes into and out from the cornea. The double pass may also include reflection from the retina. As a result, proper polarization filtering with a combination of two polarizers can allow for polarized light that has passed through the cornea and reflected from the retina to be separated from polarized light that has reflected off the front surface of the cornea. The polarized light that has reflected off the front surface of the cornea can be filtered out by a second polarizer without fully or substantially filtering out the light reflected off of the retina. The filtering of polarized light reflected off the front surface of the cornea can increase the contrast ratio of the images of the retina or other portion of the eye captured by a device or viewed by an ophthalmologist. As such, the second polarizer can separate corneal reflections (e.g., reflections from the front surface of the cornea) from retinal reflections when the incident light is properly polarized. Thus, the first polarizer and second polarizer are cooperatively configured for filtering out the corneal reflections.

The problem of corneal reflection from the anterior surface may inhibit imaging or visualization of the RPE. However, such corneal reflection from the anterior surface may inhibit imaging or visualization of the anterior region, middle region, posterior region or posterior surface of the eye. As such, the corneal reflection may be attenuated or extinguished as provided herein with the second polarization. Additionally, one or more additional light polarizers may be included to inhibit additional reflections (e.g., in addition to reflections from the corneal anterior surface at the cornea-air interface) from the eye, such as from any of the other layers of the cornea or other regions of the eye. As such, the number of additional light polarizers can be selected to optimize attenuation of the number of distinct reflections in the eye. The additional light polarizers may be selectively rotated in combination with the first polarizer (e.g., light source polarizer) of the incident light and the second polarizer (e.g., corneal light polarizer) of light reflected from the corneal anterior surface in order to attenuate or extinguish these other reflections so that the light of the desired reflection can be imaged or visualized for different procedures.

The present technology may be able to filter out reflections from one or all of the corneal layers. In instances that there are reflections from layers other than the anterior surface due to birefringence, such reflections from one or more layers may be attenuated or extinguished by a second polarization and additional subsequent polarizations of the polarized light that is reflected from the anterior surface and other regions of the cornea. Polarized light that is reflected from the eye may be polarized by a corneal light polarizer (e.g., for the anterior surface reflection) and one or more additional polarizers, such as in a polarization series. Each polarizer may have a different rotational position with respect to other polarizers in a polarization series to selectively attenuate different reflections that have different polarizations.

FIG. 1 illustrates an embodiment of an optical system 100. The optical system 100 can include a light source 102 emitting light 2 (e.g., un-polarized light) toward a light source polarizer 120 (also referred to herein as an "incident light polarizer"). The light source polarizer 120 polarizes the light 2 to a first polarized light 4 (e.g., first polarization) that is directed to an image target 114 and on to an eyepiece 199 (e.g., contact lens) before entering an eye 101. The first polarized light 4 can include a portion of light that is reflected off of the corneal anterior surface 103 of the cornea 107 and light that passes through the corneal posterior surface 105 of the cornea 107 that is reflected off of the retina 109 (e.g., epiretinal membrane 109a and/or RPE 109b). Together, all of the reflected light is reflected light 6, which includes corneal light 6a (e.g., reflected from the cornea 107, such as off of the corneal anterior surface 103) and retinal light 6b that is reflected from the retina 109 (e.g., epiretinal membrane 109a and/or RPE 109b). Due to birefringence of the eye, the corneal light 6a has a different polarization from the retinal light 6b. The reflected light 6 then passes through a corneal light polarizer 122 to be polarized to a second polarized light 8 (e.g., second polarization). Due to the difference in polarization of the corneal light 6a compared to the retinal light 6b, the corneal light 6a is polarized into second polarized light 8 having a portion that is second corneal polarized light 8a having a different polarization from the second retinal polarized light 8b. As such, the second corneal polarized light 8a may be attenuated more than the second retinal polarized light 8b, which provides for better contrast. As such, the second polarized light 8 has second corneal polarized light 8a that is more attenuated or extinguished compared to the retinal polarized light 8b.

The light source 102 can be any light source that emits light, such as a single color, multi-color, or white light. The light source 102 may emit white light, which may be from an incandescent light bulb (e.g., tungsten lamp), LED, multiple LEDs, high-intensity discharge lamp, or other source that emits visible light.

The polarizers, such as the light source polarizer 120 and corneal light polarizer 122, can be any polarizer that can polarize visible light for color imaging, such as a polarizer capable of polarizing light having a wavelength of about 400 to about 700 nm. One example of a polarizer can be an Edmund Optics 85-919 polarizer. Another example of a polarizer can be a Tiffen 72 mm Linear Polarizer. However, it should be recognized that any suitable linear or circular polarizer can be used with this technology.

FIG. 1 shows that the optical system 100 includes the light source polarizer 120 operably coupled to a rotating mechanism 130 (e.g., first rotating mechanism) so that the light source polarizer 120 can be rotated to change the polarization. Also, FIG. 1 shows the optical system 100 includes the corneal light polarizer 122 operably coupled to a rotating mechanism 130 (e.g., second rotating mechanism). However, the optical system 100 may include at least one rotating mechanism 130, wherein the at least one rotating mechanism is: coupled with the light source polarizer 120; coupled with the at least one corneal light polarizer 122; or coupled with the light source polarizer 120 and the at least one corneal light polarizer 122. As such, a rotating mechanism may not be coupled to the light source polarizer 120 or corneal light polarizer 122, so long as a rotating mechanism 130 is coupled to at least one of the light source polarizer 120 or the at least one corneal light polarizer 122.

The rotating mechanism 130 can include a member that mounts to the polarizers (e.g., 120 and/or 122). Such a mounting member can be any polarizer mount, such as, for example, Edmunds Optics 55-011 polarizer mount. Such a polarizer mount can be operably coupled to any type of motor to facilitate rotation of the polarizers.

In one aspect, the reflected light 6 can be passed through a series of polarizers 122a that includes one or more additional polarizers in addition to the corneal light polarizer. Such polarizers in the series of polarizers 122a may be rotatably coupled to a rotating mechanism 130 for being individually selectively rotated and rotationally positioned. The series of polarizers 122a may be rotationally positioned to attenuate or extinguish light reflected from other layers of the eye, such as other corneal layers.

FIG. 1 shows the optical system 100 includes a receiver 40 that is positioned and configured to receive the second polarized light 8 that has the second corneal polarized light 8a that is more attenuated or extinguished compared to the retinal polarized light 8b. The receiver 40 may be an optical receiver device, such as a light detector, charge-coupled device (CCD), camera, CMOS detector, photodiode, or any other type of image or light detecting device. One example of a receiver 40 may be a megapixel high dynamic range image sensor (e.g., VG6640, STMicroelectronics). The receiver 40 may also be an optical port that allows for direct visualization of the second polarized light 8, such as a viewing port 140 (see FIG. 4), eyepiece, objective, lens, or other visualization device to allow eye viewing.

In one embodiment, the rotating mechanisms 130 may be automated by being operably coupled to a controller 111 (e.g., a computer), which operable coupling allows for data communication between the rotating mechanism 130 and controller 111 such that the controller 111 controls the rotation and position of the light source polarizer 120 and/or corneal light polarizer 122. Such control of the rotation and position of the light source polarizer 120 and/or corneal light polarizer 122 can be used to control the polarization of the second polarized light 8 so that the second corneal polarized light 8a is more attenuated or extinguished compared to the second retinal polarized light 8b. Thus, enhanced contrast of a visualized or imaged eye can be obtained.

In one aspect, when the receiver 40 is a device, the receiver 40 may be operably coupled with the controller 111 so that data from the receiver 40 may be provided to the controller. The receiver data may then be used by the controller 111 to rotate and position the light source polarizer 120 and/or corneal light polarizer 122 to optimize the image as well as to optimize attenuation of the second corneal polarized light 8a compared to the second retinal polarized light 8b. As such, the controller 111 can have image optimization software stored on a tangible, non-transitory data storage medium as computer-executable code that can implement a process to optimize the image. Such optimization can receive data from the receiver 40, process such data, and provide data to selectively rotate at least one of the light source polarizer 120 and/or corneal light polarizer 122 until the image is optimized by having optimized contrast and/or optimized second corneal polarized light 8a attenuation or extinction.

In one aspect, the controller 111 may be operated by a professional, such as a surgeon or ophthalmologist or assistant in order to improve the optimized second corneal polarized light 8a attenuation or extinction or improve the contrast of the image.

In one aspect, the optical system 100 of FIG. 1 may include a basic optical device having the light source polarizer 120 and corneal light polarizer 122, wherein at least one of the light source polarizer 120 or corneal light polarizer 122 is rotatably coupled with a rotating mechanism 130. Such a basic optical device may be operably coupled with one or more of the light source 102, image target 114, eyepiece 199, receiver 40, and/or controller 111 in order to form the optical system 100. However, an optical device may include one or more of the light source 102, image target 114, eyepiece 199, receiver 40, and/or controller 111 in a housing. An optical device may include other components, such as objectives, lenses, lens series, mirrors, dichroic mirrors, beam splitters, detectors, laser modules or other components.

In one embodiment, the optical system can be used in improved retinal imaging, retina visualization, eye examination, eye diagnostics, and eye surgery (e.g., laser eye surgery, as R:GEN laser eye surgery, etc.).

Figure 2:
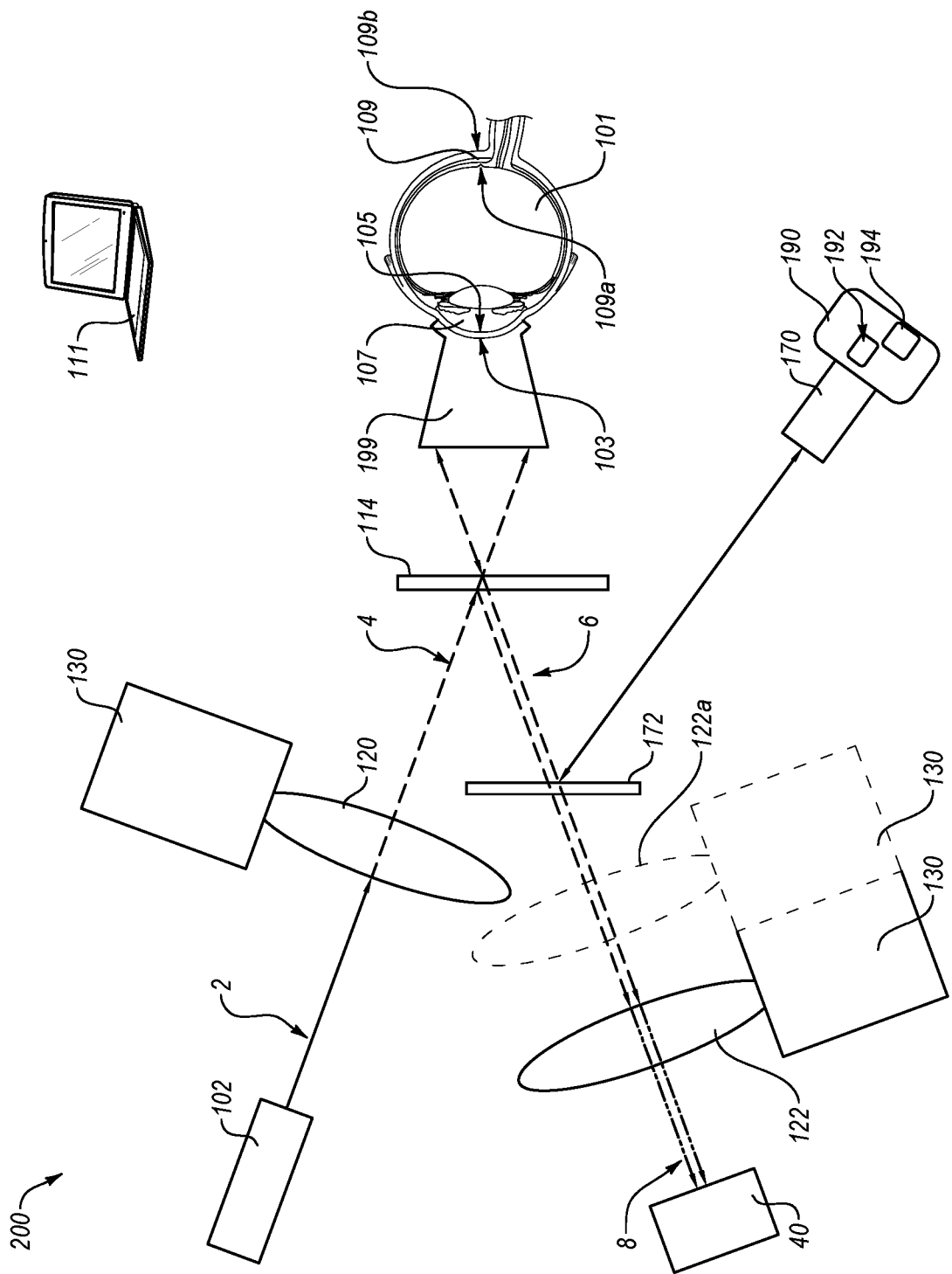
FIG. 2 illustrates an embodiment of an optical system.

FIG. 2 illustrates an embodiment of an optical system 200. Accordingly, FIG. 2 shows the optical system 200 may include the components of FIG. 1 and additionally include a laser module 190. The laser module 190 is shown to include a laser emitter 192 that is configured to emit laser light that is suitable for an optical procedure, such as laser eye surgery (e.g., as R:GEN laser eye surgery). The laser module 190 also includes a detector 194 associated with the laser emitter 192 such that the laser emitter 192 and detector have a common optical direction. Accordingly, an optical device having a housing may include the components of FIG. 2, or the components, such as the laser module 190 may be separate and operably coupled with the device in order to form the optical system. This allows the optical system 200 to be retrofit with existing optical systems and/or laser surgery systems that are used for retinal imaging, retina visualization, eye examination, eye diagnostics, and eye surgery (e.g., laser eye surgery) or other features.

Figure 3A:
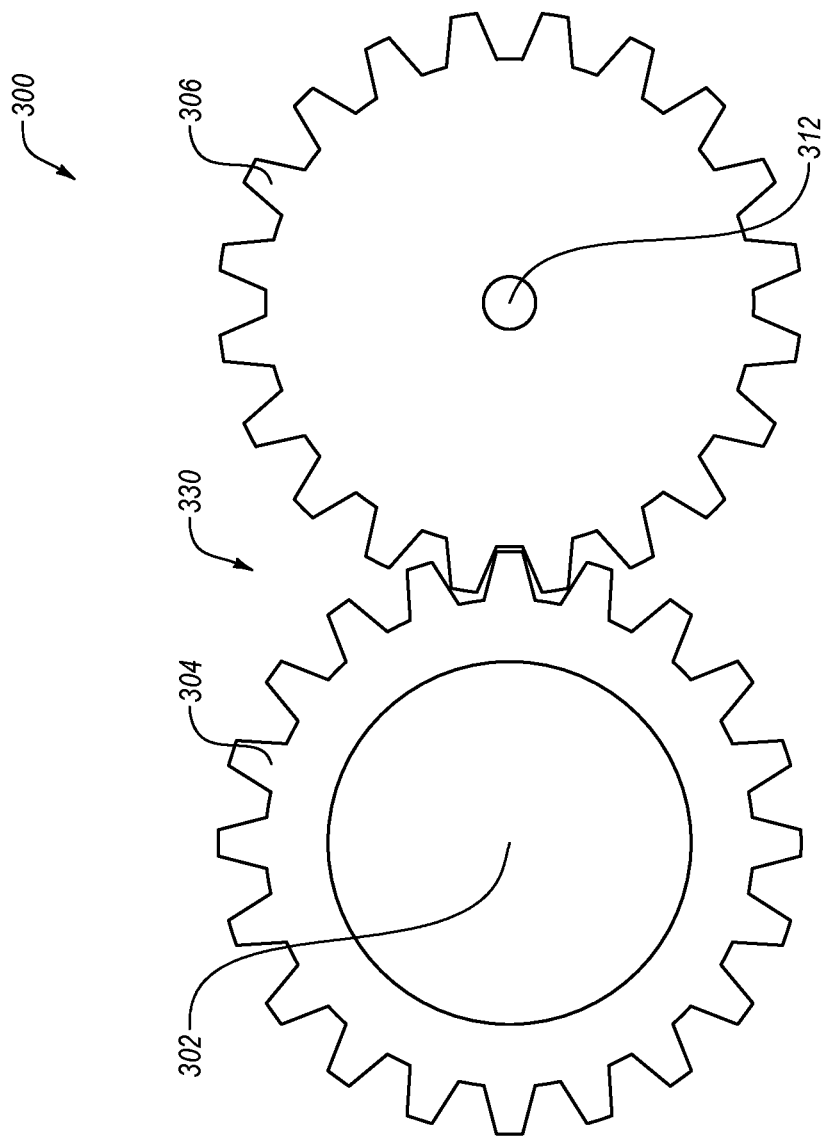
FIG. 3A illustrates a side view of an embodiment of a rotatable polarizer system.
Figure 3B:
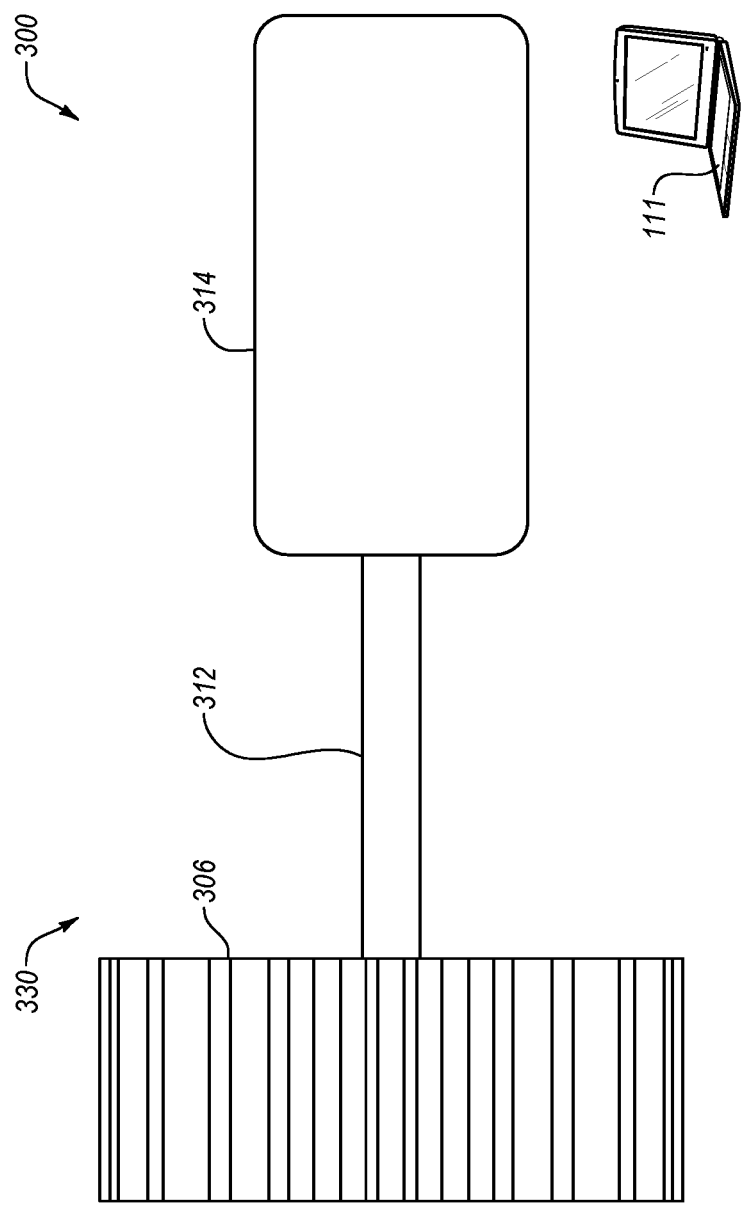
FIG. 3B illustrates an end view of an embodiment of a rotatable polarizer system.

FIGS. 3A-3B illustrate an embodiment of a rotatable polarizer system 300. FIG. 3A illustrates a side view of the rotatable polarizer system 300. FIG. 3B illustrates an end view of the rotatable polarizer system 300. The rotatable polarizer system 300 includes a polarizer 302 rotatably coupled with a rotating mechanism 330. Accordingly, the polarizer 302 can have a rotation gear 304 that is operably coupled to a drive gear 306. As shown, the polarizer 302 is circumferentially coupled into an aperture of the rotation gear 304 such that rotation of the rotation gear 304 rotates the polarizer 302. While not shown, the polarizer 302 and rotation gear 304 may be included in a track to allow for rotation thereof while maintaining an axis of rotation and not relocating within an optical device or optical system. This allows the polarizer 302 to stay within an optical path so as to polarize the light traversing the optical path. The drive gear 306 is mounted on a drive shaft 312 to allow for rotation. The rotation of the drive gear 306 rotates the polarizer 302 via rotation of the rotation gear 304. The drive gear 306 is operably coupled to a drive shaft 312 that is operably coupled to a motor 314. The motor 314 may be operably coupled with the controller 111 so that the rotational position of the polarizer 302 can be selectively changed. While the rotatable polarizer system 300 is shown to include a geared rotating mechanism 330, any type of mechanism that can rotate and position the polarizer 302 may be included in the devices and systems described herein.

The rotatable polarizer system 300 may include the polarizer 302 as the light source polarizer 120 and/or the at least one corneal light polarizer 122 as described herein. As such, the rotatable polarizer system 300 may include the light source polarizer 120 or at least one corneal light polarizer 122.

Figure 4:
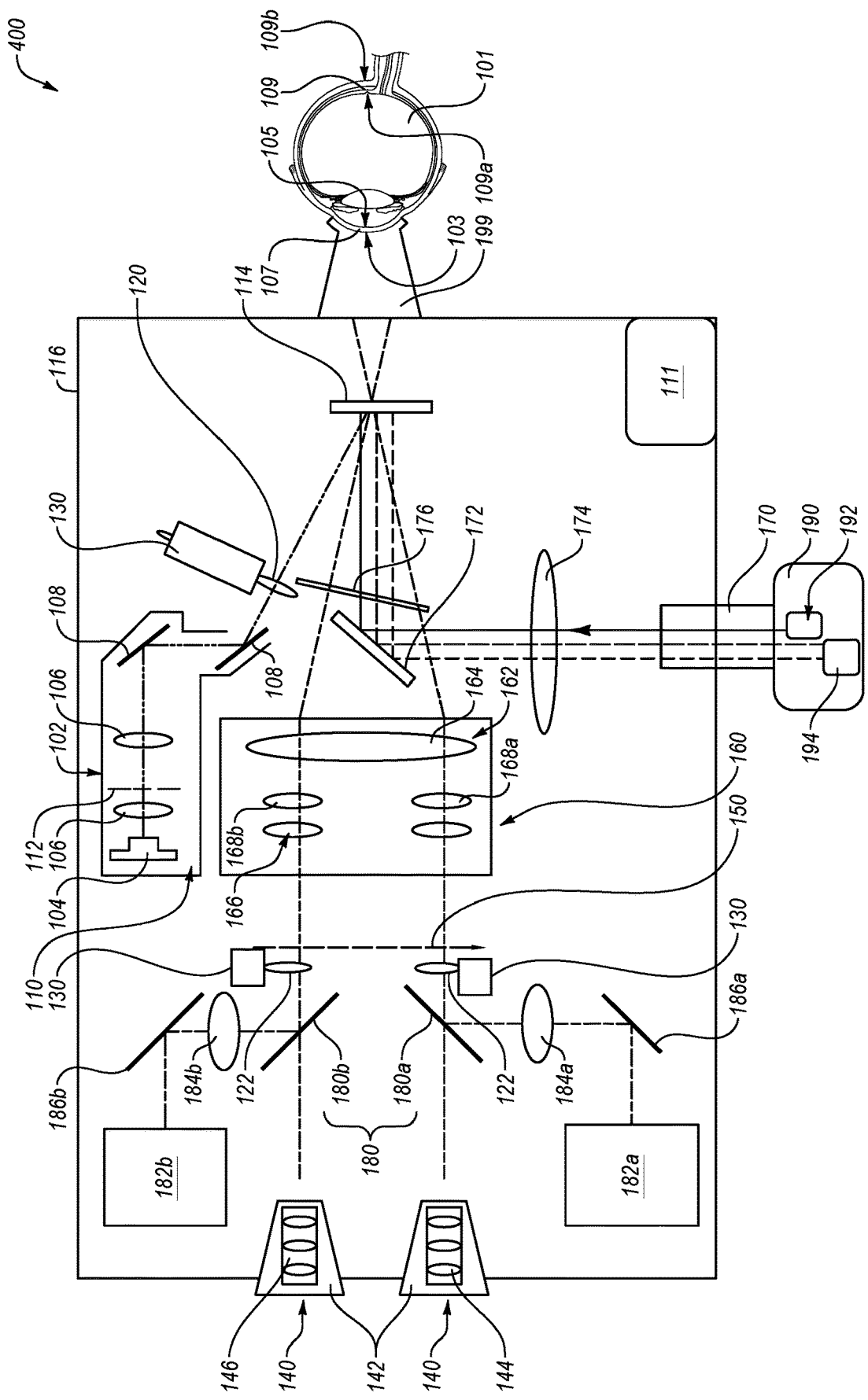
FIG. 4 illustrates an embodiment of an optical device.

FIG. 4 illustrates an embodiment of an optical device 400. The optical device 400 can be used in the methods and optical systems described herein. The components of the optical device 400 may be included with the embodiments of FIGS. 1, 2, 3A, and 3B. The optical device 400 can include a light source polarizer 120 (also referred to as an incident light polarizer) that is optically coupled with incident light, such as incident light from a light source 102. The incident light passes through the light source polarizer 120 and is polarized into first polarized light. The first polarized light then is directed toward an eye 101 of a subject. Prior to entering the eye 101, the first polarized light may pass through an image target 114, which may include a window or slit or other transparent feature to allow light to pass therethrough, and may include an opaque region bounding the transparent feature. The opaque region can inhibit light from passing therethrough and can thereby be positioned to select the light beams that can pass through the transparent feature. As such, the first polarized light can traverse the image target 114. The optical device 400 may include an eyepiece 199 as illustrated so as to be optically aligned with the image target 114 to receive the first polarized light from the light source polarizer 120. However, the eyepiece 199 can be a separate device that is coupled with a housing 116 of the optical device 400, or can be separate and usable with the optical device 400, such as by being placed adjacent and optically aligned with an aperture or optical port (not shown) in the housing 116.

Light that is reflected from the eye can then travel back through the eyepiece 199 and to at least one corneal light polarizer 122. The at least one corneal light polarizer 122 is a separate polarizer from the light source polarizer 120. In FIG. 4 there are two corneal light polarizers 122 shown; however, configurations may include one or more than two corneal light polarizers 122. The at least one corneal light polarizer 122 is positioned to receive reflected light from the cornea of the subject, and is configured to polarize the reflected light to a second polarization (e.g., second polarized light). The optical device 400 can include at least one rotating mechanism 130 that is configured to rotate a polarizer, such as at least one of a light source polarizer 120 or corneal light polarizer 122. Accordingly, the at least one rotating mechanism can be: coupled with the light source polarizer 120; coupled with the at least one corneal light polarizer 122; or coupled with the light source polarizer 120 and the at least one corneal light polarizer 122 as shown in FIG. 4. As shown, the optical device includes at least one viewing port 140 (e.g., two viewing ports 140 are shown) optically coupled with the at least one corneal light polarizer 122; however, one or both of the viewing ports 140 may be substituted with a different type of receiver 40 (FIGS. 1 and 2), such as a light detector. The optical device 400 may also include other components in various arrangements as described below. However, it should be recognized that some or all of the components, such as those also listed heretofore may be optional, such as the light source 102, image target 114, eyepiece 199, or others.

In one embodiment, the light source polarizer 120 is configured to polarize incident light from a light source 102 to a first polarization in an illumination path directed to a cornea 107 of a subject. The at least one corneal light polarizer 122 is positioned to receive reflected light from the cornea 107 and retina 109 of a subject and polarize the reflected light to a second polarization, wherein the reflected light is from the light source 102 and light source polarizer 120. It should be noted that the light reflected from the cornea 107 and retina 109 may also include light reflected from other aspects of the eye; however, reference to light reflected from the cornea 107 and retina 109 is used for simplicity and illustration of the optical device 400 even though the light from the eye 101 may include various portions each with a unique polarization due to birefringence of the eye 101.

As indicated, a rotating mechanism 130 can be coupled with the light source polarizer 120 without a rotating mechanism 130 coupled with a corneal light polarizer 122. Alternatively, a rotating mechanism 130 can be coupled with the at least one corneal light polarizer 122 without a rotating mechanism 130 coupled with the light source polarizer 120. In yet another alternative, the at least one rotating mechanism includes a first rotating mechanism 130 coupled with the light source polarizer 120 and includes at least one second rotating mechanism 130 that is coupled with the at least one corneal light polarizer 122.

As shown in FIG. 4, the at least one viewing port 140 includes at least one ocular piece 142 for viewing through with an eye. Each ocular piece 142 of the at least one ocular piece 142 can include at least one lens 144. Also, an ocular objective 146 having the at least one lens 144 may be included. In one aspect, the at least one viewing port 140 is configured for viewing with an eye 101.

The optical device 400 can include a housing 116 that retains the light source 102 therein so as to be an integral part of the optical device 400. However, it should be recognized that the housing 116 may include an optical port to allow for a separate and external light source 102 to be used with the optical device. A light emitter 104 can be located in the light source 102. In one aspect, the light source is a light emitting diode (LED), halogen light, high intensity discharge lamp, light bulb, or any other light emitter that emits light usable for imaging an eye 101. In one aspect, at least one lens 106 can be included in the light source 102 that is optically coupled with the light emitter 104. The lens 106 can be any type of lens, such as a focusing lens, defocusing lens, magnifying lens, collimating lens, or the like. Depending on the configuration, at least one mirror 108 can be included in the light source 102 that is optically coupled with the light emitter 104. Such a mirror 108 may allow for the positioning of the light emitter 104 to be optimized. In one example, at least one mirror 108 is located in the light source 102 so as to be optically coupled with the light emitter 104 and the at least one lens 106. In one aspect, an optical aperture device 112 having an optical aperture can be located in the light source 102 so as to be optically coupled with the light emitter 104. The light source 102 can include a housing 110 containing the light emitter 104 and optionally including the other components of the light source.

As indicated herein, the optical device 400 can include an image target 114 having an image target aperture, wherein the light source polarizer 120 is between the image target 114 and the light source 102. Also, a housing 116 can be included that contains the light source polarizer 120, the at least one corneal light polarizer 122, and the at least one rotating mechanism 130, as well as any of the other components.

The optical device 400 can also include at least one safety filter 150 positioned such that the reflected light passes through the at least one safety filter 150 before the at least one viewing port 140 or other receiver 40. In one aspect, the at least one corneal light polarizer 122 is between the at least one safety filter 150 and the at least one viewing port 140 or other receiver 40. In one aspect, the at least one safety filter 150 is between the at least one corneal light polarizer 122 and the at least one viewing port 140 or other receiver 40. The safety filter 150 can be a high optical density optical filter with a spot band at the wavelength of a treatment laser, such as a Vbeam Filter (e.g., T5B06, Laservision).

An optical objective 160 can be positioned such that the reflected light passes through the optical objective 160 before the at least one viewing port 140 or other receiver 40. The optical objective 160 can be positioned such that the reflected light passes through the optical objective 160 before the at least one corneal light polarizer 122.

A lens 162 can be positioned such that the reflected light passes through the lens 162 before the at least one viewing port 140 or other receiver 40. The lens 162 can be positioned such that the reflected light passes through the lens 162 before the at least one corneal light polarizer 122. In one aspect, a convergent lens 164 can be positioned such that the reflected light passes through the convergent lens 164 before the at least one viewing port 140. In one aspect, the convergent lens 164 can be positioned such that the reflected light passes through the convergent lens 164 before the at least one corneal light polarizer 122. In one aspect, a lens series 166 can be included, and may have a convergent lens 164. The lens series 166 can include: at least one right eye lens 168a positioned such that the reflected light passes through the convergent lens 164 and the at least one right eye lens 168a before a right eye viewing port of the at least one viewing port 140; and at least one left eye lens 168b positioned such that the reflected light passes through the convergent lens 164 and the at least one left eye lens 168b before a left eye viewing port of the at least one viewing port 140. A lens series 166 may also include: at least one right eye lens 168a positioned such that the reflected light passes through the convergent lens 164 and the at least one right eye lens 168a before the at least one corneal light polarizer 122; and at least one left eye lens 168b positioned such that the reflected light passes through the convergent lens 164 and the at least one left eye lens 168b before the at least one corneal light polarizer 122.

The optical device 400 may be used for passive viewing or diagnostics within implementing a process or procedure (e.g., laser eye surgery) to the eye 101. However, the optical device may include or be configured to operably couple with a laser module 190. As such, the optical device 400 may include a laser port 170 positioned to receive the reflected light from the eye 101 (e.g., cornea 107 or retina 109) of the subject. The optical device 400 can include a laser mirror 172 positioned to receive the reflected light from the eye 101 (e.g., cornea 107) of the subject and reflect the reflected light to the laser port 170. The optical device 400 can include a collimating lens 174 positioned to receive the reflected light from the cornea of the subject and configured to provide collimated light to the laser port 170.

The optical device 400 can include a controller 111 operably coupled with the at least one rotating mechanism 130. The controller 111 can be configured to control rotation of the at least one rotating mechanism 130 so as to control rotation of one of: the light source polarizer 120; the at least one corneal light polarizer 122; or the light source polarizer 120 and the at least one corneal light polarizer 122 independently of each other.

The optical device 400 can include a window 176 positioned to receive the reflected light from the cornea of the subject. Such a window 176 can be positioned such that the reflected light passes through the window 176 before at least one of an optical objective 160, convergent lens 164, lens series 166, right eye lens 168a, left eye lens 168b, or laser mirror 172. The window 176 can be a BK7 glass window (e.g., Edmund Optics 45-076).

The optical device 400 can include at least one beam splitter 180 that is positioned between the at least one corneal light polarizer 122 and at least one viewing port 140 or other receiver 40. At least one detector 182 can be positioned such that a split portion of the reflected light from the cornea of the subject that is split by the at least one beam splitter 180 is received by the at least one detector 182. In one aspect, the at least one beam splitter 180 includes a right eye beam splitter 180a and a left eye beam splitter 180b and the at least one detector 182 includes a near infrared detector 182a and a color detector 182b. In one aspect, the optical device 400 can include at least one of the following: a right collimating lens 184a between the right eye beam splitter 180a and one of the near infrared detector 182a and color detector 182b; a right mirror 186a between the right eye beam splitter 180a and one of the near infrared detector 182a and color detector 182b; a left collimating lens 184b between the left eye beam splitter 180b and one of the near infrared detector 182a and color detector 182b; or a left mirror 186b between the left eye beam splitter 180b and one of the near infrared detector 182a and color detector 182b. The beam splitter 180 may be any beam splitter relative to the wavelength of light, such as with a range of 400-700 nm (e.g., Edmund Optics 48-915).

The near infrared detector 182a and color detector 182b may be operably coupled with the controller 111 so that data can be provided to the controller 111 for processing to determine the rotational position of the light source polarizer 120 and/or the at least one corneal light polarizer 122 in order to attenuate or extinguish the reflection from the corneal anterior surface 103. The controller 111 may include a computer processor and a tangible, non-transitory storage medium with executable instructions for operating and acquiring data from the near infrared detector 182a and color detector 182b, processing the data, and controlling the at least one rotating mechanism to selectively rotate and position the light source polarizer 120 and/or the at least one corneal light polarizer 122.

In one embodiment, wherein the light source polarizer 120 is a linear polarizer. Also, the at least one corneal light polarizer 122 can be a linear polarizer. Alternatively, the light source polarizer 120 is a circular polarizer. In another alternative, the at least one corneal light polarizer 122 is a circular polarizer.

In one embodiment, the light source polarizer 120 is coupled with the at least one rotating mechanism 130 and the at least one corneal light polarizer 122 is fixed and not rotatable. Alternatively, the at least one corneal light polarizer 122 is coupled with the at least one rotating mechanism 130 and the light source polarizer 120 is fixed and not rotatable.

In one embodiment, the optical device 400 can include a laser module 190, which can be integrated with the housing 116, can be physically coupled with the housing 116, can be included within the housing 116, which can be external to the housing, or which can be operably coupled but physically separate from the housing. As such, the optical device 400 can be retrofit to an existing laser module 190 that is configured for laser eye surgery. Laser module 190 can include a laser emitter 192. The laser module 190 can also include a detector 194 associated with the laser emitter 192 such that the laser emitter 192 and detector have a common optical direction.

In one embodiment, the optical device 400 can include an eyepiece 199 adapted for association with an eye 101 of the subject, the eye 101 having the cornea 107. The eyepiece 199 can be integrated with the housing 116, can be physically coupled with the housing 116, can be included within the housing 116, which can be external to the housing, or which can be operably coupled but physically separate from the housing.

In one embodiment, an optical device 400 can include: a light source polarizer 120 optically coupled with incident light (e.g., light source 102); at least one corneal light polarizer 122, wherein the at least one corneal light polarizer 122 is positioned to receive reflected light from the cornea of the subject and polarize the reflected light to a second polarization; at least one rotating mechanism 130; and a laser port 170 operably coupled to a laser module 190.

In one embodiment, the optical device 400 can include: a light source polarizer 120 optically coupled with incident light (e.g., light source 102); at least one corneal light polarizer 122, wherein the at least one corneal light polarizer 122 is positioned to receive reflected light from the cornea of the subject and polarize the reflected light to a second polarization; and at least one rotating mechanism 130, wherein the at least one rotating mechanism is coupled with the light source polarizer 120.

In one embodiment, the optical device 400 can include: a light source polarizer 120 optically coupled with incident light (e.g., light source 102); at least one corneal light polarizer 122, wherein the at least one corneal light polarizer 122 is positioned to receive reflected light from the cornea of the subject and polarize the reflected light to a second polarization; and at least one rotating mechanism 130, wherein the at least one rotating mechanism is coupled with the light source polarizer 120 and the at least one corneal light polarizer 122.

In one embodiment, the optical device 400 can include the laser module 190, and eyepiece 199 adapted for association with an eye of the subject.

In one embodiment, a laser procedure system can include the optical device of one of the embodiments, and a separate eyepiece 199 adapted for association with an eye of the subject. In another embodiment, a laser procedure system can include: the optical device of one of the embodiments; a laser module 190; and an eyepiece 199 adapted for association with an eye of the subject.

The optical device or system having the optical device can be used in various methods or medical procedures that utilize visualization or imaging of an eye. The methods or medical procedures can include laser eye surgery, such as R:GEN laser eye surgery. In one embodiment, a laser eye surgery method can include providing the optical device of one of the embodiments, and associating the optical device with an eye 101 of the subject. The method can include directing the polarized light with the first polarization to a cornea 107 (e.g., corneal anterior surface 103 and/or to a corneal posterior surface 105) and to a retina 109 of the eye 101. The method can include receiving the reflected light from the cornea 107 (e.g., corneal anterior surface 103 and/or from the corneal posterior surface 105) and from the retina 109 into the at least one corneal light polarizer 122. The reflected light from the cornea 107 (e.g., corneal anterior surface 103 and/or corneal posterior surface 105) has the first polarization and the reflected light from the retina 109 has a different polarization from the first polarization, in part, due to birefringence of the eye. The method can include polarizing the reflected light from the cornea 107 having the first polarization with the at least one corneal light polarizer 122 so as to obtain attenuated corneal light and polarizing the reflected light from the retina 109 having the different polarization with the at least one corneal light polarizer 122 so as to obtain attenuated retinal light. The configuration of the polarizers can result in the attenuated corneal light having less intensity that the attenuated retinal light.

In one aspect, the light source polarizer is positioned to have a polarization direction that is crossed with a polarization direction of the at least one corneal light polarizer so that the attenuated corneal light is substantially attenuated or extinguished. However, the light source polarizer and at least one corneal light polarizer may have various relative positions or undergo changes in positions in order to optimize attenuation of the corneal reflected light. In one aspect, the method can include rotating the light source polarizer 120 and/or rotating the at least one corneal light polarizer 122. Such rotation can be selected to a desired attenuation level of the corneal reflected light and retinal reflected light. For example, the method can include independently rotating the light source polarizer 120 and independently rotating the corneal light polarizer 122.

In one embodiment, the method can include marking a target position of the eye 101, such as marking the cornea 107 (e.g., corneal anterior surface 103 and/or corneal posterior surface 105) or retina 109 (e.g., epiretinal membrane 109a and/or RPE 109b). In one aspect, the retina 109 (e.g., epiretinal membrane 109a and/or RPE 109b) is marked. In one aspect, the cornea 107 (e.g., corneal anterior surface 103 and/or corneal posterior surface 105) is not marked. In one aspect, the marking is done with the controller. In one aspect, the method can include positioning a laser module 190 relative to the marked target position of the eye 101 (e.g., cornea 107 or retina 109). In one aspect, the method can include performing laser eye surgery on the eye 101 (e.g., on the retina 109) with the laser module 190. In one aspect, marking the target position of the eye can include applying a treatment laser (e.g., CW laser) to photocoagulate the irradiated region to change the optics in the eye.

In one embodiment, the method can include adjusting a polarization angle of the polarized light by rotating the light source polarizer 120 and/or rotating the corneal light polarizer 122. Such rotation can result in increasing the contrast of an image of the retina by adjusting a difference in intensity of the attenuated corneal light compared to the attenuated retinal light. Also, such rotation can result in filtering out the corneal light with the at least one corneal light polarizer 122. In one aspect, the rotation may be under automatic control of the controller 111 in response to data regarding the image, such as contrast data.

Additionally, the optical devices described herein may be used for methods that involve visualizing or imaging the eye with improvements by attenuating light reflected by the cornea. Accordingly, the optical devices may be used in a method of improving eye image contrast during eye imaging. The method can include associating the optical device with an eye 101 of the subject, the eye having the cornea 107 and retina 109. The method can include directing the polarized light from the light source polarizer 120 with the first polarization to the cornea 107 (e.g., corneal anterior surface 103 and/or a corneal posterior surface 105) and to the retina 109 (e.g., epiretinal membrane 109a and/or RPE 109b). The method can include receiving the reflected light from the cornea 107 (e.g., corneal anterior surface 103 and from the corneal posterior surface 105) and from the retina 109 (e.g., epiretinal membrane 109a and/or RPE 109b) into the at least one corneal light polarizer 122, wherein the reflected light from the cornea 107 has the first polarization and the reflected light from the retina 109 has a different polarization from the first polarization. The method can include polarizing the reflected light from the cornea 107 having the first polarization with the at least one corneal light polarizer 122 so as to obtain attenuated corneal light and polarizing the reflected light from the retina 109 having the different polarization with the at least one corneal light polarizer 122 so as to obtain attenuated retinal light, such that the attenuated corneal light has less intensity than the attenuated retinal light. In one aspect, light source polarizer 120 has a polarization direction that is crossed with a polarization direction of the at least one corneal light polarizer 122 so that the attenuated corneal light is substantially attenuated or extinguished. The method can include rotating the light source polarizer 120 to vary the relative polarization of the reflected light to improve attenuation or extinguishment of the reflected light. The method may also or alternatively include rotating the at least one corneal light polarizer 122 to vary the relative polarization of the reflected light to improve attenuation or extinguishment of the reflected light. Also, the method can include independently rotating the light source polarizer 120 and independently rotating the corneal light polarizer 122 to vary the relative polarization of the reflected light to improve attenuation or extinguishment of the reflected light. In one aspect, the method can include marking a target position of the eye 101 (e.g., cornea 107 or retina 109). In one aspect, the method can include adjusting a polarization angle of the polarized light by rotating the light source polarizer 120 without rotating the at least one corneal light polarizer 122. In one embodiment, the method can include increasing the contrast of an image of the retina by adjusting a difference in intensity of the attenuated corneal light compared to the attenuated retinal light. In one embodiment, the method can include filtering out the corneal light with the at least one corneal light polarizer 122. In one embodiment, the different steps of the method can be automated under the control of the controller 111.

In one embodiment, the attenuation of light reflections from a cornea by a second polarization can improve contrast in optical imaging or eye viewing of the retina. While such improved contrast during imaging or viewing can be helpful during any eye procedure, such as eye examination, eye diagnostics, and eye surgery (e.g., laser eye surgery, R:GEN, etc.) or others. In an example, such improved contrast can be beneficial during R:GEN laser treatment by filtering out light reflected from the surface of the cornea. The method is performed by taking advantage of the birefringent character of the eye (e.g., cornea). In a majority of patients, polarized light entering the cornea will rotate due to the birefringent properties of the cornea, with the median rotation of about 20° for a double-pass of light (e.g., light passing through the cornea, reflecting off of the retina and passing through the cornea again). As a result, double polarization filtering allows polarized light that has entered the cornea to be separated from polarized light that has reflected off the surface of the eye, thereby increasing the contrast ratio of the images obtained by detector devices or viewed by surgeons.

In one embodiment, the optical device can be used with an R:GEN laser system, which is a surgical laser instrument for use by ophthalmic physicians for performing selective retinal therapy (SRT) for treatment of clinically significant macular edema (CSME), which is a condition secondary to diabetic retinopathy. In one aspect, the device can be used for diagnosing macular edema (CSME) and/or diabetic retinopathy by improved contrast in the imaging or visualization.

In one embodiment, the optical device and laser module can be used for laser photocoagulation of the retina by laser-targeting the outer layers as a therapy for proliferative retinopathy and macular edema from diabetic microangiopathy or retinal vein occlusion, central serous retinopathy, and extrafoveal subretinal neovascular membranes. In one aspect, the device can be used for diagnosing diabetic microangiopathy or retinal vein occlusion, central serous retinopathy, and extrafoveal subretinal neovascular membranes by improved contrast in the imaging or visualization.

In one embodiment, the optical device and laser module can be used for laser treatments of the macula, where the therapeutic effect results from stimulation of the retinal pigment epithelium cells with the laser. Accordingly, the optical device may be used for imaging and viewing the macula by improved contrast in the imaging or visualization.

In one embodiment, the optical device can be used for automated detection of a microbubble response of RPE cells with a sensor (e.g., 194 or other sensor) during R:GEN, which treats the retina with laser treatment without damage to the photoreceptor. As such, the optical device may be used for patients with macular diseases that may lead to blindness, and thereby may inhibit onset or progression of blindness.

In one embodiment, an R:GEN system (e.g., Lutronic) is provided. Then, a rotatable polarizer is included in the R:GEN system in front of the illumination unit (e.g., light source), so that polarized light enters the cornea during use. Additionally, additional polarization filter(s) (e.g., optionally rotatable) are placed into the optical path after the light exits the cornea. In one example, a single rotatable polarizer can be included in the illumination path, which rotatable polarizer can be used to adjust the polarization angle of the incident light in order to optimize contrast ratio of an image from light reflected from the eye. The rotatable polarizers may be rotated in order to tune the light reflected from the eye to an acceptable contrast and intensity. The rotation of the rotatable polarizers can be performed to adjust to the birefringence of each individual patient. Additional polarizers are positioned between the safety filter and the ocular piece (e.g. view port), to minimize the intensity of light incident on the eyes of the ophthalmologist or eye surgeon or other medical professional. This positioning allows dichroic filters to be used.

However, alternative placements of the rotatable polarizers are possible, such as the one or more corneal light polarizers can be made rotatable (e.g., while the polarizer in the illumination path is made fixed). In another alternative, the two corneal light polarizers 122 (e.g., one for each eye of the medical professional) shown in FIG. 4 after the safety filter 150 can be replaced with a single wire polarizer in the return optical path. In another embodiment, the polarizers can be circular polarizers rather than linear polarizers. For simplicity, all of the examples herein refer to linear polarized light; however, the implementation of circularly polarized light is similar.

In one embodiment, the optical device and methods of use take advantage of the natural birefringence of the eye to isolate the optical image of the back of the eye (e.g., retina) from unwanted reflections off the cornea. Polarized light is passed from the illumination unit to the eye, and reflections off the air-cornea interface maintain this initial polarization (e.g., first polarization). Meanwhile, light that enters the eye will rotate in polarization because of the eye's birefringence. When this polarized light exits the eye, its polarization will significantly differ from the input polarized light. These two differently polarized beams can be separated using a second polarizer (e.g., corneal light polarizer) in the return path of the optics of the optical device. For example, intensity of light coming through a pair of crossed polarizers is determined by the Law of Malus, which states that when a perfect polarizer is placed in a polarized beam of light, the intensity, I, of the light that passes through is given by the following equation.

$$I = I0 \cos 2(\theta)$$

Figure 5A:
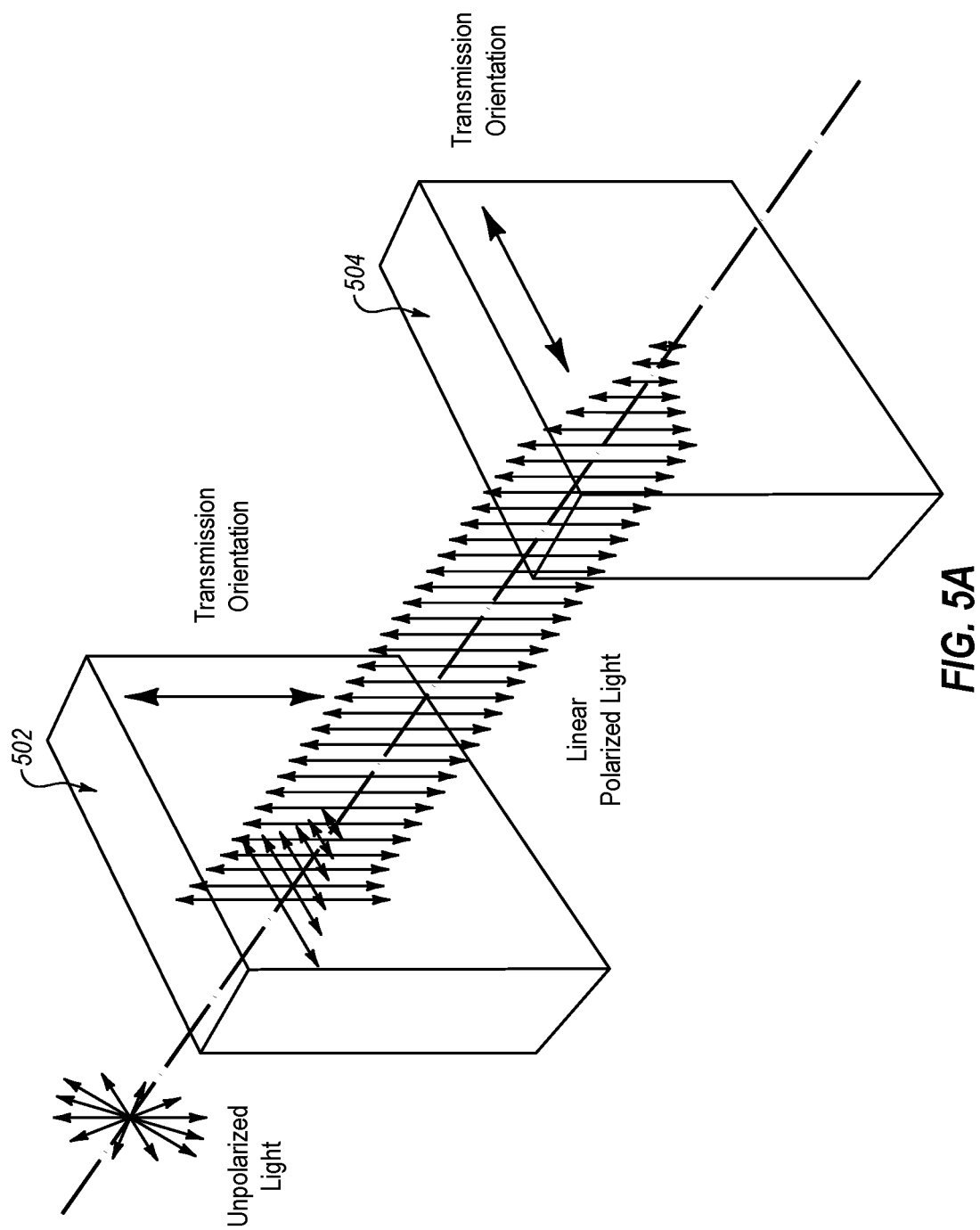
FIG. 5A illustrates a schematic of an embodiment of a polarizer system.
Figure 5B:
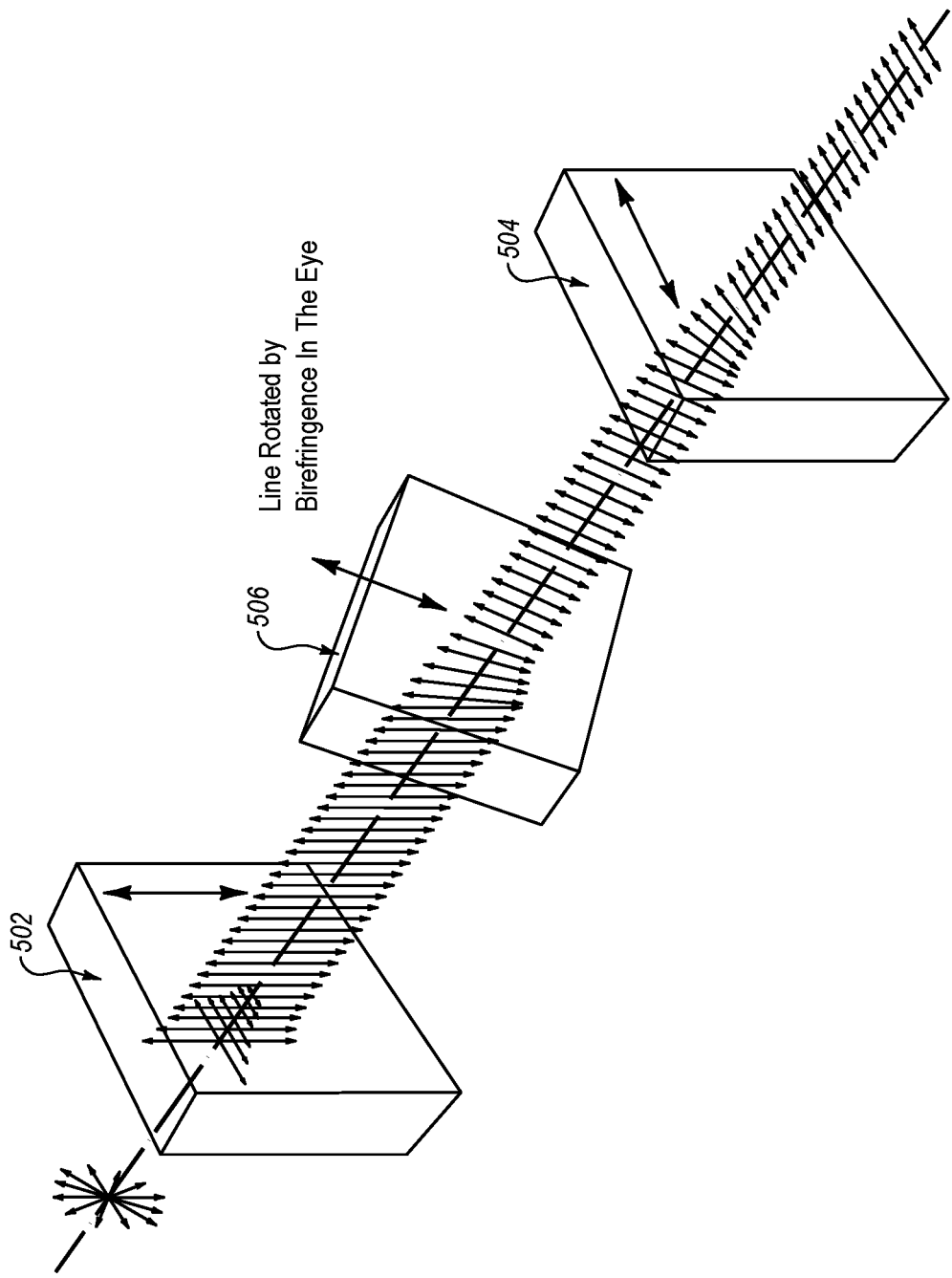
FIG. 5B illustrates a schematic of an embodiment of a polarizer system with an example of eye birefringence.

Here, I0 is the initial intensity, and θ is the angle between the initial polarization direction of the incident light and the axis of the polarizer. Note that all calculations assume ideal polarizers; however, the performance of real materials may be slightly lower. Also, normal incidence of the light is assumed in this model. The polarizers can be rotatable to give the medical professional control over both intensity of light and contrast for the eyes of a specific patient. However, there is a tradeoff between intensity and attenuation of light reflected from the cornea. FIG. 5A illustrates a schematic of an embodiment of a polarizer system. In a first embodiment shown in FIG. 5A, a second polarizer 504 is at 90° relative to a first polarizer 502, which are positioned to be "crossed polarizers". Polarized light from the first polarizer 502 hits the eye and reflects off the air-cornea interface and its polarization does not change, and then its intensity is extinguished by the crossed second polarizer 504, as illustrated in FIG. 5A. FIG. 5B illustrates a schematic of an embodiment of a polarizer system with an example of eye birefringence. In FIG. 5B, the polarized light is rotated by the eye 506 before it impinges on the second, crossed polarizer 504. As a result, some of this light is able to pass through as shown, but it is attenuated. The desired light that is reflected off the back of the eye 506 can be obtained with a reduced intensity or none of the unwanted reflections off the air-cornea interface.

However, perfect exclusion of unwanted reflections using crossed polarizers can result in a loss of some of the intensity of the desired light. In a first example, a patient has eyes 506 that rotate linearly polarized light by 20°. If the first and second polarizers (502, 504, respectively) are crossed at a 90° angle, none of the unwanted reflections will get through the second polarizer 504, but the desired image will be attenuated to 12% of its initial intensity. However, there is improved contrast of the image. This is an improvement, and with the addition of the ability to adjust source light intensity the resulting image can be sufficient enough for the medical professional to see the desired structure (e.g., RPE). In a second example, second polarizer 504 is set at 70° relative to the first polarizer 502. Now, the unwanted reflected light from the cornea is attenuated to 12%, but the desired light from the retina is only attenuated to 41%. As a result, there is some contrast degradation relative to the first example, but there is much higher intensity of the light for the desired image. In one aspect, any amount of polarization may be used. In one aspect, an important factor can be the contrast ratio, and the ability to have enough light available at the image plane (e.g., by the optometrist, detector, etc.) to be useful.

It has been found that a difference in polarizer angles between the first polarizer and second polarizer above 50° significantly improve contrast ratio. It has been found that a difference in polarizer angle between the first polarizer and second polarizer being 80° results in the contrast ratio increasing by a factor of 2-10. Accordingly, rotatable polarizers can be used to optimize the difference in polarization angles for patients with specific birefringence. It is thought that selectively rotating the polarizers can obtain improvements in the contrast ratio increasing by a factor of 20 times or more. A rotatable polarizer can allow for a medical professional to tailor the polarization for the patient. Even with small birefringence, the optimal polarization angle between the two polarizers has a fairly broad window (e.g., wide width at half max in the peaks), which means that polarization can use fairly coarse adjustments. Also, this allows for the medical professional to optimize intensity and contrast ratio for an individual patient.

However, it is possible for the polarization filter to be fixed, for example at an angle of +70°. In this case, however, it may be desirable to make the polarizers removable from the path.

For this and other processes and methods disclosed herein, the operations performed in the processes and methods may be implemented in differing order. Furthermore, the outlined operations are only provided as examples, and some operations may be optional, combined into fewer operations, eliminated, supplemented with further operations, or expanded into additional operations, without detracting from the essence of the disclosed embodiments.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. The terminology used herein is for the purpose of describing particular embodiments only, and is not intended to be limiting.

In one embodiment, the present methods can include aspects performed on a computing system. As such, the computing system can include a memory device that has the computer-executable instructions for performing the methods. The computer-executable instructions can be part of a computer program product that includes one or more algorithms for performing any of the methods of any of the claims.

In one embodiment, any of the operations, processes, or methods, described herein can be performed or cause to be performed in response to execution of computer-readable instructions stored on a computer-readable medium and executable by one or more processors. The computer-readable instructions can be executed by a processor of a wide range of computing systems from desktop computing systems, portable computing systems, tablet computing systems, hand-held computing systems, as well as network elements, and/or any other computing device. The computer readable medium is not transitory. The computer readable medium is a physical medium having the computer-readable instructions stored therein so as to be physically readable from the physical medium by the computer/processor.

There are various vehicles by which processes and/or systems and/or other technologies described herein can be effected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The various operations described herein can be implemented, individually and/or collectively, by a wide range of hardware, software, firmware, or virtually any combination thereof. In one embodiment, several portions of the subject matter described herein may be implemented via application specific integrated circuits (ASICs), field programmable gate arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware are possible in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a physical signal bearing medium include, but are not limited to, the following: a recordable type medium such as a floppy disk, a hard disk drive (HDD), a compact disc (CD), a digital versatile disc (DVD), a digital tape, a computer memory, or any other physical medium that is not transitory or a transmission. Examples of physical media having computer-readable instructions omit transitory or transmission type media such as a digital and/or an analog communication medium (e.g., a fiber optic cable, a waveguide, a wired communication link, a wireless communication link, etc.).

It is common to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. A typical data processing system generally includes one or more of a system unit housing, a video display device, a memory such as volatile and non-volatile memory, processors such as microprocessors and digital signal processors, computational entities such as operating systems, drivers, graphical user interfaces, and application programs, one or more interaction devices, such as a touch pad or screen, and/or control systems, including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. Such depicted architectures are merely exemplary, and that in fact, many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include, but are not limited to: physically mateable and/or physically interacting components and/or wirelessly interactable and/or wirelessly interacting components and/or logically interacting and/or logically interactable components.

Figure 6:
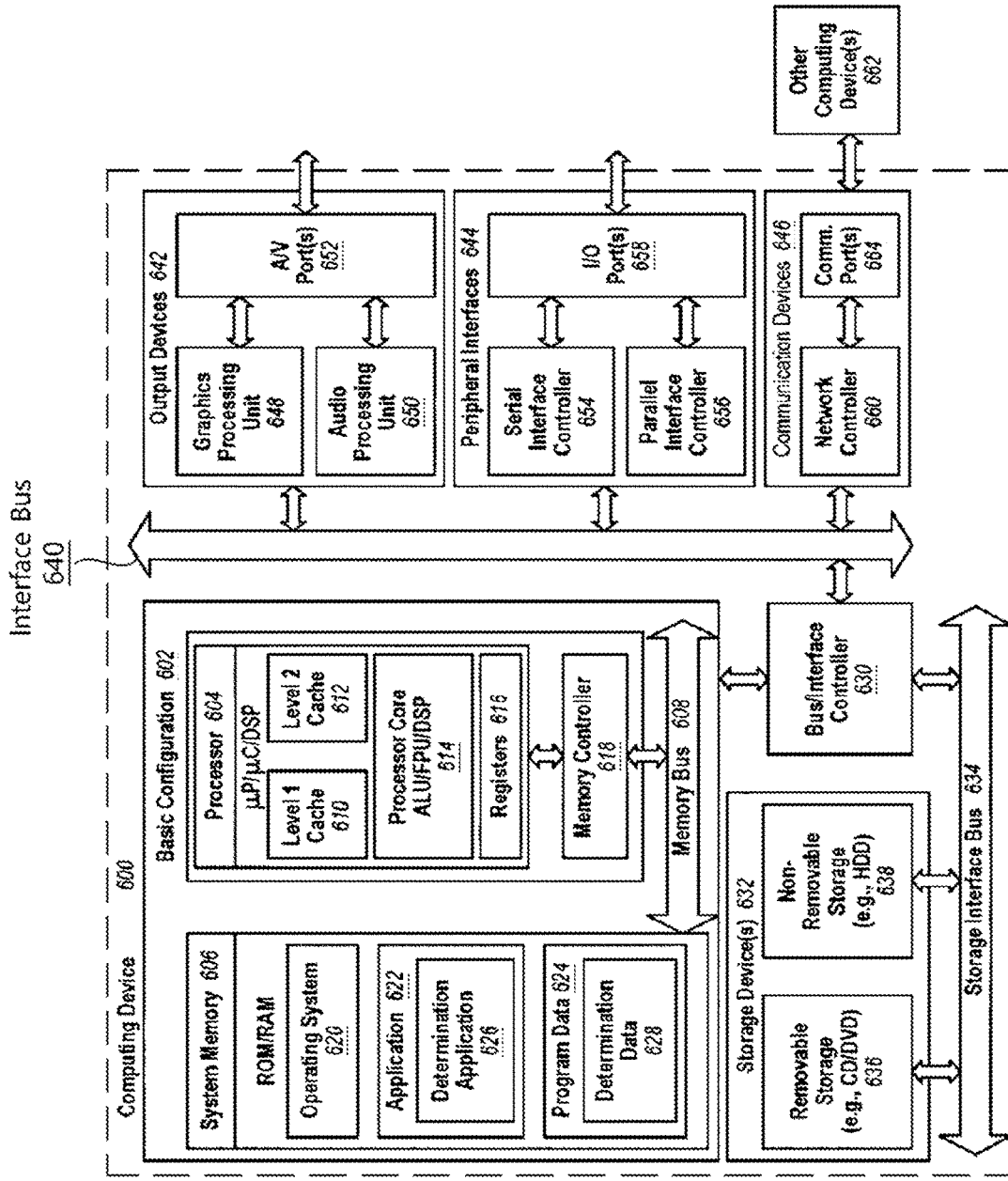
FIG. 6 shows an example computing device.

FIG. 6 shows an example computing device 600. The computing device 600 may be arranged in some embodiments to perform the methods (or portions thereof) described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including, but not limited to: a microprocessor (µP), a microcontroller (µC), a digital signal processor (DSP), or any combination thereof. Processor 604 may include one or more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations, memory controller 618 may be an internal part of processor 604.

Depending on the desired configuration, system memory 606 may be of any type including, but not limited to: volatile memory (such as RAM), non-volatile memory (such as ROM, flash memory, etc.), or any combination thereof. System memory 606 may include an operating system 620, one or more applications 622, and program data 624. Application 622 may include a determination application 626 that is arranged to perform the operations as described herein, with determination data 628, including those described with respect to methods described herein.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include: magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include: volatile and nonvolatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to: RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" can refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. An optical device comprising:
an incident light polarizer positioned to polarize incident light that is directed to a cornea and a retina of a subject, wherein the polarized incident light has a first polarization;
at least one corneal light polarizer positioned to polarize corneal light reflected from the cornea to obtain attenuated corneal light and polarize retinal light reflected from the retina to obtain attenuated retinal light, wherein the attenuated corneal light has less intensity than the attenuated retinal light;
a first rotating mechanism coupled with the incident light polarizer so as to adjust a polarization of the incident light to direct to the cornea and the retina;
at least one second rotating mechanism coupled with the at least one corneal light polarizer; and
at least one viewing port optically coupled with the at least one corneal light polarizer.

2. The optical device of claim 1, wherein the at least one viewing port includes at least one eyepiece.

3. The optical device of claim 1, further comprising a light source configured to provide the incident light.

4. The optical device of claim 1, further comprising at least one safety filter positioned such that the reflected light passes through the at least one safety filter before the at least one viewing port.

5. The optical device of claim 1, further comprising a convergent lens positioned such that the reflected light passes through the convergent lens before the at least one viewing port.

6. The optical device of claim 1, further comprising:
a convergent lens;
at least one right eye lens positioned such that the reflected light passes through the convergent lens and the at least one right eye lens; and
at least one left eye lens positioned such that the reflected light passes through the convergent lens and the at least one left eye lens.

7. The optical device of claim 1, further comprising:
a mirror positioned to reflect a portion of the reflected light; and
a laser port positioned to receive the reflected portion of the reflected light from the mirror.

8. The optical device of claim 1, further comprising a controller operably coupled with the first rotating mechanism and the at least one second rotating mechanism, wherein the controller is configured to control rotation of
the incident light polarizer and the at least one corneal light polarizer independently of each other.

9. The optical device of claim 1, further comprising:
at least one beam splitter positioned between the at least one corneal light polarizer and at least one viewing port; and
at least one detector positioned such that a split portion of the reflected light from the cornea of the subject by the at least one beam splitter is received by the at least one detector, wherein the at least one detector includes at least one of a near infrared detector or a color detector.

10. The optical device of claim 1, wherein at least one of the incident light polarizer or the at least one corneal light polarizer is a linear polarizer.

11. The optical device of claim 1, wherein at least one of the incident light polarizer or the at least one corneal light polarizer is a circular polarizer.

12. The optical device of claim 1, further comprising:
a mirror positioned to reflect a portion of the reflected light;
a laser port positioned to receive the reflected portion of the reflected light from the mirror; and
a laser module having a laser emitter and a detector optically coupled with the laser port to receive the reflected light from the laser.

13. A laser procedure system comprising:
an optical device comprising:
an incident light polarizer positioned to polarize incident light that is directed to a cornea and a retina of a subject, wherein the polarized incident light has a first polarization;
at least one corneal light polarizer positioned to polarize corneal light reflected from the cornea to obtain attenuated corneal light and polarize retinal light reflected from the retina to obtain attenuated retinal light, wherein the attenuated corneal light has less intensity than the attenuated retinal light;
a first rotating mechanism coupled with the incident light polarizer so as to adjust a polarization of the incident light to direct to the cornea and the retina;
at least one second rotating mechanism coupled with the at least one corneal light polarizer; and
at least one viewing port optically coupled with the at least one corneal light polarizer;
an eyepiece adapted for association with an eye of the subject; and
a laser module optically coupled with the eyepiece,
wherein the first rotating mechanism includes a rotation gear and a drive gear, the rotation gear having an aperture to which the incident light polarizer is coupled, the rotation gear being operably coupled to the drive gear, the drive gear being operably coupled to a drive shaft.

* * * * *